US012594042B2

(12) United States Patent     (10) Patent No.:   US 12,594,042 B2

Meyer et al.     (45) Date of Patent:     Apr. 7, 2026

(54) DEVICE FOR MOVING A MEDICAL OBJECT AND METHOD FOR PROVIDING A CORRECTION PRESET

(71) Applicant: Siemens Healthcare GmbH, Erlangen (DE)

(72) Inventors: Andreas Meyer, Bubenreuth (DE); Michael Wiets, Langensendelbach (DE); Christian Kaethner, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 747 days.

(21) Appl. No.: 17/679,067

(22) Filed: Feb. 23, 2022

(65) Prior Publication Data

US 2022/0265230 A1     Aug. 25, 2022

(30) Foreign Application Priority Data

Feb. 24, 2021   (DE) ..................... 10 2021 201 727.4

(51) Int. Cl.
| | |
|---|---|
| *A61B 6/04* | (2006.01) |
| *A61B 6/00* | (2024.01) |
| *A61B 34/20* | (2016.01) |

(52) U.S. Cl.
CPC .......... *A61B 6/0487* (2020.08); *A61B 6/0407* (2013.01); *A61B 6/4458* (2013.01); *A61B 6/447* (2013.01); *A61B 6/547* (2013.01); *A61B 2034/2065* (2016.02)

(58) Field of Classification Search
CPC ... A61B 6/0487; A61B 6/0407; A61B 6/4458; A61B 6/447; A61B 6/547; A61B 2034/2065
See application file for complete search history.

(56) References Cited

U.S. PATENT DOCUMENTS

| | | |
|---|---|---|
| 7,974,681 B2 | 7/2011 | Wallace et al. |
| 9,237,930 B2 | 1/2016 | Hauck |

(Continued)

FOREIGN PATENT DOCUMENTS

| | | |
|---|---|---|
| CN | 107468265 A | 12/2017 |
| JP | 2004033652 A | 2/2004 |
| JP | 2015150206 A | 8/2015 |

*Primary Examiner* — Sean A Frith

(74) *Attorney, Agent, or Firm* — Lempia Summerfield Katz LLC

(57) ABSTRACT

A device for moving a medical object includes a mover device for robotically moving the medical object. At least a predefined section of the medical object is arranged in an examination subject in an operating state of the device. The device is configured to receive a control preset. The control preset specifies a first movement for the predefined section of the medical object. The mover device is configured to move the medical object along a first movement direction in accordance with the control preset. The device is further configured to identify a deviation between a movement state of the predefined section of the medical object and the first movement and to determine a correction preset in order to minimize the deviation. The mover device is further configured to move the medical object at least partially counter to the first movement direction in accordance with the correction preset.

16 Claims, 8 Drawing Sheets

(56)                 References Cited

U.S. PATENT DOCUMENTS

2013/0204124 A1 *   8/2013   Duindam ............... A61B 5/065
                                                    604/272
2013/0345718 A1 *  12/2013   Crawford ............... A61B 34/76
                                                    606/130
2015/0045812 A1     2/2015   Seo
2016/0287134 A1 *  10/2016   Foong ................... A61B 34/20
2017/0151027 A1 *   6/2017   Walker ................. A61B 34/37
2017/0265952 A1 *   9/2017   Donhowe ............. A61B 34/30
2017/0281145 A1    10/2017   Crawford et al.
2017/0354385 A1    12/2017   Lerch
2019/0008599 A1 *   1/2019   Lynch ................... A61B 34/32
2019/0105117 A1 *   4/2019   Brisson ................. A61B 34/30
2020/0129740 A1     4/2020   Kottenstette et al.
2020/0405375 A1 *  12/2020   Shelton, IV ....... A61B 18/1815

* cited by examiner

DEVICE FOR MOVING A MEDICAL OBJECT AND METHOD FOR PROVIDING A CORRECTION PRESET

This application claims the benefit of German Patent Application No. DE 10 2021 201 727.4, filed on Feb. 24, 2021, which is hereby incorporated by reference in its entirety.

BACKGROUND

The present embodiments relates to a device for moving a medical object, a system, a method for providing a correction preset, a method for providing a trained function, and a computer program product.

Interventional medical procedures in or across a vascular system of an examination subject frequently require a medical object (e.g., an elongate medical instrument) to be introduced (e.g., percutaneously) into the vascular system. Further, in order to provide successful diagnosis and/or treatment, it is often necessary to guide at least a part of the medical object forward toward a target region that is to be treated in the vascular system.

During a movement of the medical object (e.g., a translation and/or rotation), it may happen that the medical object (e.g., a distal end portion of the medical object) is impeded in its movement. For example, the movement of the medical object may be obstructed by a structure of the examination subject along the movement direction of the medical object (e.g., a tissue of the examination subject and/or an occlusion and/or a stenosis). In order to overcome such an obstacle, the medical object may be moved manually (e.g., while being monitored by X-ray fluoroscopy). A disadvantageous aspect in this situation is the increased exposure to radiation and the heightened risk of injury for the examination subject, for example, due to a perforation of a tissue. A medical operator moving the medical object is often exposed to an increased level of radiation.

SUMMARY AND DESCRIPTION

The scope of the present invention is defined solely by the appended claims and is not affected to any degree by the statements within this summary.

The present embodiments may obviate one or more of the drawbacks or limitations in the related art. For example, obstacles along a movement trajectory of a medical object may be overcome in a safe and time-efficient manner.

The present embodiments relate, in a first aspect, to a device for moving a medical object. The device includes a mover device for robotically moving the medical object. Further, at least a predefined section of the medical object is arranged in an examination subject (e.g., a hollow organ of the examination subject) in an operating state of the device. The device is further embodied for receiving a control preset (e.g., a control instruction). The control preset specifies a first movement for the predefined section of the medical object. In addition, the mover device is embodied to move the medical object along a first movement direction in accordance with the control preset. The device is further embodied to identify a deviation between a movement state of the predefined section of the medical object and the first movement, and to determine a correction preset (e.g., a correction instruction) in order to minimize the deviation. The mover device is further embodied in this case to move the medical object at least partially counter to the first movement direction in accordance with the correction preset.

The medical object may be embodied in this case, for example, as a surgical and/or diagnostic instrument (e.g., elongate). For example, the medical object may be flexible and/or rigid, at least in sections. The medical object may be embodied, for example, as a catheter and/or an endoscope and/or a guide wire.

In one embodiment, the mover device may be a robotic device that is embodied to allow remote manipulation of the medical object (e.g., a catheter robot). The mover device may be arranged outside of the examination subject. Further, the mover device may include a securing element (e.g., movable and/or displaceable). The mover device may also include a cassette element that is configured to accommodate at least a part of the medical object. The mover device may also include a mover element that is fixedly mounted on the securing element (e.g., a stand and/or a robotic arm). The securing element may also be embodied to secure the mover element to a patient support and positioning device. In addition, the mover element may include at least one actuator element (e.g., an electric motor) that is controllable by a provisioning unit. In one embodiment, the cassette element may be couplable (e.g., mechanically and/or electromagnetically and/or pneumatically) to the mover element (e.g., to the at least one actuator element). In this case, the cassette element may also include at least one transmission element that is movable owing to the coupling between the cassette element and the mover element (e.g., the at least one actuator element). For example, the at least one transmission element may be movably coupled to the at least one actuator element. In one embodiment, the transmission element is embodied to transmit a movement of the actuator element to the medical object such that the medical object is moved along a longitudinal extension direction of the medical object and/or the medical object is rotated around a longitudinal extension direction of the medical object. The at least one transmission element may include, for example, a roller and/or drum and/or shield and/or shearing plate that is embodied to transmit a force onto the medical object. The transmission element may be further embodied to halt (e.g., hold) the medical object (e.g., in a stable manner) by transmitting the force. The halting of the medical object may, for example, include a stationary positioning of the medical object in relation to the mover device.

The mover element may include a plurality of actuator elements (e.g., independently controllable). The cassette element may further include a plurality of transmission elements (e.g., at least one movably coupled transmission element for each of the actuator elements). This may facilitate a movement (e.g., an, in independent and/or simultaneous) of the medical object along different degrees of freedom.

The medical object may be introduced by an introducer sheath at least partially into the examination subject such that the predefined section (e.g., a distal end portion) of the medical object (e.g., a tip) is arranged inside the examination subject. The predefined section may, for example, describe an end portion (e.g., distal end portion) of the medical object (e.g., a tip). The predefined section may be predetermined as a function of the medical object and/or of the examination region and/or be defined by an input by an operator. The examination subject may be, for example, a human and/or animal patient and/or a vessel phantom. Further, the examination subject may have a hollow organ (e.g., a vessel section, such as a vein and/or an artery, and/or a heart and/or a lung), in which the predefined section (e.g., the distal end portion) of the medical object may be arranged.

The device may further include a provisioning unit that is embodied to control the device and/or components of the control device (e.g., the mover device). The device (e.g., the provisioning unit) may be embodied to receive the control preset. The receiving of the control preset may, for example, include an acquisition thereof and/or a readout thereof from a computer-readable data memory and/or a receiving thereof from a data storage unit (e.g., a database). Further, the control preset may be provided by an input unit for acquiring an input by an operator. The control preset may include at least one command for a control (e.g., incremental control) of the mover device. For example, the control preset may include at least one command (e.g., a temporal sequence of commands) for specifying the first movement of the predefined section of the medical object. The first movement may in this case include, for example, a translation and/or rotation (e.g., simultaneous translation and rotation) of the medical object (e.g., of the predefined section) using the mover device. The provisioning unit may be embodied to translate the control preset and to control the mover device based thereon. The mover device may also be embodied to move the medical object along a first movement direction (e.g., translationally and/or rotationally) in accordance with the control preset.

The first movement direction may describe a spatial dimension along which the medical object is essentially to be moved in accordance with the control preset (e.g., relative to the mover device and/or relative to a longitudinal extension direction of the medical object). For example, the first movement direction may be a resulting movement direction and/or main movement direction of the medical object relative to the mover device. To the extent that the medical object is embodied at least in sections as flexible, the predefined section of the medical object inside the examination subject (e.g., inside the hollow organ) may follow a spatial (e.g., curved) course of a tissue of the examination subject (e.g., a longitudinal extension direction of the hollow organ). The first movement of the predefined section may include, for example, a feed-forward movement and/or a withdrawal movement and/or a rotational movement. The feed-forward movement may describe a movement of the medical object directed substantially away from the mover device (e.g., a distal movement). Further, the withdrawal movement may describe a movement of the medical object directed substantially toward the mover device (e.g., a proximal movement). The rotational movement may describe a rotation of the medical object around a longitudinal extension direction of the medical object. For example, the first movement may be a movement composed of different spatial movement components. The preset specified for the first movement for the predefined section of the medical object may include a preset (e.g., an instructions) specified for the first movement direction and/or for a first movement speed for the medical object (e.g., relative to the mover device in each case and/or relative to a longitudinal extension direction of the medical object).

Alternatively or in addition, the control preset may include a preset (e.g., an instruction) specified with regard to a spatial target positioning to be reached by the predefined section of the medical object (e.g., a spatial position and/or orientation and/or pose to be reached) in the examination subject. In this case, the provisioning unit may be embodied to translate the control preset into at least one command for controlling the mover device (e.g., based on an image and/or a model of the examination subject), and to control the mover device based thereon. For example, the provisioning unit may be embodied to control the mover device based on the control preset such that the predefined section of the medical object is moved along the first movement direction into the target positioning.

The device may be further embodied to identify the deviation between the movement state (e.g., current movement state) of the predefined section of the medical object and the first movement. The movement state of the predefined section may, in this case, describe a movement direction and/or movement speed (e.g., current) of the predefined section (e.g., vectorially). The device (e.g., the provisioning unit) may also be embodied to identify the deviation using a comparison between the specified first movement (e.g., based on the control preset) and the movement state (e.g., current movement state) of the predefined section.

For example, the device may be embodied to receive information relating to a spatial positioning (e.g., current spatial positioning) of the predefined section of the medical object. The device may be further embodied in this case to determine the deviation using a comparison between the spatial positioning (e.g., current spatial positioning) specified by the control preset and the actual spatial positioning (e.g., current spatial positioning) of the predefined section. The device may also be embodied to determine the deviation using a comparison between a relative speed of the medical object in relation to the mover device and a movement speed of the predefined section. The determining of the deviation (e.g., the respective comparison) may, in this case, include a determining of a difference and/or a quotient, in which case the difference and/or the quotient may be compared further with a first predetermined threshold value. In this regard, the first predetermined threshold value may be specified as a function of the medical object (e.g., of a material parameter and/or operating parameter of the medical object, such as based on a user input and/or by an artificial intelligence process).

Further, the device may be embodied to determine the correction preset for minimizing the deviation. The correction preset may, in this case, include, (e.g., analogously to the control preset) at least one command for control (e.g., incremental control) of the mover device. For example, the correction preset may include at least one command (e.g., a temporal sequence of commands) for specifying translation and/or rotation (e.g., simultaneous translation and/or rotation) of the medical object (e.g., of the predefined section) by the mover device. In one embodiment, the device may be embodied to determine the correction preset such that the deviation between the movement state (e.g., current movement state) of the predefined section of the medical object and the first movement is minimized. For this purpose, the correction preset may include the at least one command for specifying a corrective movement of the predefined section of the medical object. In one embodiment, the mover device may be embodied to move the medical object at least partially counter to the first movement direction in accordance with the correction preset. Further, following the completed corrective movement in accordance with the correction preset, the device may be embodied to move the medical object once again according to the, for example, original and/or an adjusted control preset. For this purpose, the correction preset may further include information relating to the control preset (e.g., original and/or adjusted). This enables the first movement in accordance with the control preset to be continued following the corrective movement.

The device may be embodied to conduct repeated checks to determine whether the deviation between the movement state (e.g., current movement state) of the predefined section of the medical object and the first movement is present. Further, the device may be embodied to determine the correction preset repeatedly.

The device may enable an obstacle along the first movement direction of the medical object to be overcome in an improved (e.g., time-efficient and/or X-ray-dose-efficient) manner.

In a further embodiment of the device, the mover device may be embodied to halt and/or to move the medical object by transmission of a force. The device may also be embodied to receive a signal from a sensor unit. In this case, the sensor unit may be embodied to detect a counterforce acting in the opposite direction to the force and to provide the signal as a function of the counterforce. The device may also be embodied to identify the deviation based on the signal.

The sensor unit may include a force transducer that is embodied to detect a counterforce exerted by the medical object and/or a structure of the examination subject on the force transducer. The sensor unit may, for example, include an electromagnetic (e.g., capacitive and/or resistive and/or piezoelectric and/or electrodynamic and/or mechanical and/or optical force transducer). The sensor unit may be at least partially integrated into the mover device and/or be arranged at a distal end portion of the medical object. The counterforce may be caused, for example, when a distal end portion of the medical object (e.g., the predefined section) comes into contact with a structure of the examination subject along the movement direction of the medical object (e.g., makes contact with a tissue of the examination subject, such as a wall of the hollow organ, and/or an occlusion, such as a thrombus, and/or a stenosis). The counterforce may also be caused by friction between a surface of the medical object and a tissue of the examination subject (e.g., a wall of the hollow organ). In this case, the counterforce may act in the opposite direction to the force for halting and/or moving (e.g., for translating and/or rotating) the medical object.

The sensor unit (e.g., the force transducer) may be embodied to provide the signal as a function of the detected counterforce. In this case, the signal may include information relating to a direction and/or a magnitude of the detected counterforce. The sensor signal may also be time-resolved. The signal may also include an operating parameter of the mover device and/or an operating parameter of the medical object and/or a physiological parameter of the examination subject (e.g., as metadata).

Further, the device may be embodied to identify the deviation based on the signal. For example, the device may be embodied to identify an occurrence of and/or a change in the counterforce based on the signal. The device may, for example, be embodied to identify the deviation when a further predetermined threshold value is reached and/or exceeded by the counterforce based on the signal. In this case, the further predetermined threshold value may be specified as a function of the medical object (e.g., of a material parameter and/or an operating parameter of the medical object, such as based on a user input and/or by an artificial intelligence process).

By this, the device may be embodied to identify the deviation, for example, without additional imaging and/or detection of the spatial positioning (e.g., current spatial positioning) of the predefined section.

In a further embodiment of the device, the sensor unit may be at least partially integrated into the mover device. In this case, the sensor unit may be embodied to detect the counterforce exerted by the medical object on the mover device. For example, the sensor unit may be at least partially integrated into the actuator element and/or the transmission element (e.g., as a torque sensor). By this, the sensor unit may be embodied to detect the counterforce exerted by the medical object (e.g., in total) on the mover device (e.g., on the actuator element and/or the transmission element).

As a result, the device may be embodied to detect a total counterforce as the counterforce exerted on the mover device by the part of the medical object arranged in the examination subject in the operating state of the device. The total counterforce may in this case include, for example, all counterforces (e.g., added together) that act on the part of the medical object arranged in the examination subject in the operating state of the device.

In a further embodiment of the device, the sensor unit may be arranged at a distal end portion of the medical object (e.g., at the predefined section). In this case, the sensor unit may be embodied to detect the counterforce exerted by a structure of the examination subject on the distal end portion of the medical object. For example, the sensor unit may be at least partially integrated into the medical object at the distal end portion. The sensor unit may be embodied to detect the counterforce exerted by the structure of the examination subject on the distal end portion (e.g., on the predefined section of the medical object, such as independently of the remaining part of the medical object).

In a further embodiment of the device, the mover device may be embodied to move the medical object along the first movement direction in accordance with the control preset such that the predefined section of the medical object executes a feed-forward movement and/or rotational movement. The mover device may be further embodied to move the medical object in accordance with the correction preset at least partially counter to the first movement direction such that the predefined section of the medical object executes a withdrawal movement and/or counterrotational movement.

The rotational movement may describe a rotation of the medical object around a longitudinal extension direction of the medical object in a first direction of rotation. The counterrotational movement may describe a rotation of the medical object around a longitudinal extension direction of the medical object counter to the first direction of rotation. The movement of the medical object (e.g., of the predefined section) in accordance with the control preset may include an isolated movement and/or a sequence of at least partially different partial movements and/or a movement composed of a plurality of at least partially different partial movements. In this case, the partial movements may include, for example, the feed-forward movement and/or rotational movement. Further, the isolated movement may describe a movement of the medical object (e.g., of the predefined section) along precisely one degree of freedom of movement.

Analogously thereto, the corrective movement of the medical object in accordance with the correction preset may include an isolated corrective movement and/or a sequence of at least partially different partial corrective movements and/or a corrective movement composed of a plurality of at least partially different partial corrective movements (e.g., a withdrawal and counterrotational movement). The partial corrective movements may in this case include, for example, the withdrawal movement and/or counterrotational movement. The isolated corrective movement may further describe a movement of the medical object (e.g., of the predefined section) counter to the degree of freedom of movement.

Further, the movement parameters of the movement and/or partial movements and/or corrective movement and/or partial corrective movement may be at least partially different (e.g., a movement speed and/or a movement direction and/or a movement duration and/or a movement distance and/or an angle of rotation).

The proposed embodiment may enable a targeted corrective movement of the medical object (e.g., of the predefined section) for subsequently overcoming the obstacle when continuing the first movement.

In a further embodiment of the proposed device, the device may be further embodied to receive information relating to a physiological movement of the examination subject. The device may be further embodied to identify the deviation taking the physiological movement into account.

The physiological movement may include, for example, a periodic and/or non-periodic movement of at least a part of the examination subject (e.g., a respiratory movement and/or cardiac movement). The device may be embodied to receive a further signal containing the information relating to the physiological movement of the examination subject from a further sensor unit. The further sensor unit may include, for example, an optical and/or electromagnetic and/or mechanical and/or acoustic sensor that is embodied to detect the physiological movement of the examination subject. Alternatively or in addition, the device may be embodied to receive the information relating to the physiological movement of the examination subject from a medical imaging device.

In one embodiment, the device may be embodied to identify the deviation such that in this case, a proportion of the deviation caused by the physiological movement of the examination subject may be compensated for. Further, an improved sensitivity and/or specificity and/or stability for the identification of the deviation may be made possible as a result.

In a further embodiment of the proposed device, the device may be further embodied to receive positioning information relating to spatial positioning (e.g., current spatial positioning) of the predefined section of the medical object. The device may be further embodied to identify the deviation using a comparison of the positioning information with the control preset.

The device and/or the medical object may, for example, include an acquisition unit that is embodied to detect the spatial positioning (e.g., current spatial positioning) of the predefined section of the medical object. In this case, the acquisition unit may be embodied to detect the spatial positioning of the predefined section absolutely (e.g., in a coordinate system of the examination subject) and/or relatively (e.g., in relation to the mover device). The acquisition unit may be further embodied to provide the positioning information containing information relating to the, for example, current spatial positioning of the predefined section. The acquisition unit may, for example, include a tracking system (e.g., electromagnetic and/or optical) and/or a medical imaging device.

This may enable the deviation to be identified precisely and in a reliable manner.

In a further embodiment of the proposed device, the device may be embodied to receive a dataset containing an image and/or a model of the examination region. The device may be further embodied to determine the positioning information and/or the correction preset based on the dataset.

The dataset may include medical image data acquired by a medical imaging device. In this case, the medical image data may contain an image of the examination region (e.g., preoperative and/or intraoperative). For example, the dataset may contain a contrast-enhanced and/or segmented image of the examination region (e.g., of the hollow organ). In this case, the image of the examination region may be spatially resolved two-dimensionally (2D) and/or three-dimensionally (3D). The image of the examination region may also be time-resolved. In one embodiment, the device may be embodied to receive the dataset (e.g., the medical image data; in real time) from the medical imaging device. In one embodiment, the dataset (e.g., the medical image data) may be registered with the coordinate system of the examination subject and/or with the mover device. The medical imaging device may be embodied as an X-ray device (e.g., a C-arm X-ray device) and/or a magnetic resonance system (MRT) and/or a computed tomography system (CT) and/or an ultrasound device and/or a positron-emission tomography system (PET).

Alternatively or in addition, the dataset may contain a 2D and/or 3D model (e.g., a centerline model and/or a volume model, such as a volume mesh model) of the examination region (e.g., of the hollow organ).

In one embodiment, the dataset may further contain an image of the predefined section in the examination region. In this case, the device may be embodied to localize the predefined section in the dataset. Localizing the predefined section in the dataset may in this case include identifying (e.g., segmenting) image elements of the dataset. The image elements image the predefined section. For example, the device may be embodied to identify the predefined section in the dataset based on a contour and/or marker structure of the predefined section. The device may also be embodied to localize the predefined section relative to the coordinate system of the examination subject and/or relative to the mover device based on the dataset (e.g., based on a registration between the dataset and the respective coordinate system). The device may also be embodied to determine (e.g., in addition to the spatial position of the predefined section) an orientation and/or pose of the predefined section based on the dataset. For this purpose, the device may be embodied to determine a spatial course of the predefined section based on the dataset.

The device may also be embodied to determine the correction preset based on the dataset (e.g., taking into account a spatial course and/or a spatial extent of the hollow organ). This may enable the correction preset to be determined for a time-efficient and/or limited corrective movement. The dataset may further contain information relating to an orifice (e.g., an ostium) and/or a branch point (e.g., a bifurcation) on the hollow organ. The medical object (e.g., the predefined section) may further have a pose (e.g., be pre-curved). In one embodiment, the device may be embodied to determine the correction preset based on the dataset such that the predefined section may be prevented from binding and/or snagging in an orifice and/or branch of the hollow organ (e.g., during the corrective movement and/or when continuing the first movement).

The present embodiments relate, in a second aspect, to a system including a proposed device and an acquisition unit. In this case, the acquisition unit is embodied to acquire the positioning information and provide the positioning information to the device.

The advantages of the proposed system substantially correspond to the advantages of the proposed device. Features, advantages, or alternative embodiments mentioned in this context may equally be applied also to the other claimed subject matters, and vice versa.

In this case, the acquisition unit may, for example, be embodied to acquire the spatial positioning of the predefined section absolutely (e.g., in a coordinate system of the examination subject) and/or relatively (e.g., relative to the mover device). The acquisition unit may be further embodied to provide the positioning information containing information relating to the, for example, current spatial positioning of the predefined section. The acquisition unit may, for example, include a tracking system (e.g., electromagnetic and/or optical) and/or a camera system and/or a medical imaging device.

In a further embodiment of the proposed system, the acquisition unit may be embodied as a medical imaging device. In this case, the medical imaging device may be embodied to acquire the dataset and provide the dataset to the device.

The medical imaging device may be embodied as an X-ray device (e.g., a C-arm X-ray device, and/or a magnetic resonance system (MRT) and/or a computed tomography system (CT) and/or an ultrasound device and/or a positron-emission tomography system (PET)). The system may further include an interface that is embodied to provide the dataset to the device (e.g., to the provisioning unit).

Methods and devices for providing a correction preset and methods and devices for providing a trained function are described hereinbelow. Features, advantages, and alternative embodiments of data structures and/or functions in methods and devices for providing a correction preset may in this case be applied to analogous data structures and/or functions in methods and devices for providing a trained function. Analogous data structures may be characterized in this context, for example, by the use of the prefix "training". Further, the trained functions used in methods and devices for providing a correction preset may have been adjusted and/or provided, for example, by methods and devices for providing a trained function.

The present embodiments relate, in a third aspect, to a method for providing a correction preset. Prior to the start of the method, a first movement of a medical object has taken place along a first movement direction by a mover device. In this case, the mover device is embodied to halt and/or move the medical object arranged at least partially in the mover device by transmitting a force in accordance with a control preset. Further, at least a predefined section of the medical object is arranged in an examination subject. In a first act of the proposed method, a control preset is received. In this case, the control preset has specified the first movement for the predefined section of the medical object prior to the start of the method. In a second act, positioning information relating to a spatial positioning of the predefined section of the medical object is received and/or determined. Alternatively or in addition, a signal containing information relating to a counterforce acting in the opposite direction to the force is received. In a third act, a deviation between a movement state of the predefined section of the medical object and that of the first movement is identified based on the signal and/or dataset. In a fourth act, the correction preset containing information for minimizing the deviation is determined. The correction preset is provided in a fifth act.

The advantages of the proposed method for providing a correction preset substantially correspond to the advantages of the proposed device for moving a medical object and/or the proposed system. Features, advantages, or alternative embodiments mentioned in this context may equally be applied also to the other claimed subject matters, and vice versa.

The receiving of the control preset and/or of the positioning information and/or of the signal may, for example, include an acquisition thereof and/or a readout thereof from a computer-readable data storage medium and/or a receiving thereof from a data storage unit (e.g., a database).

In this case, the control preset may be provided by an input unit for acquiring an input by an operator. In one embodiment, the control preset may have specified a first movement for the predefined section of the medical object prior to the start of the method. Further, the positioning information may be provided by an acquisition unit (e.g., a medical imaging device). In this case, the acquisition unit may be embodied for acquiring a spatial positioning of the predefined section. The signal may be provided by a sensor unit for detecting the counterforce. In this case, the sensor unit may be embodied to detect the counterforce exerted by the medical object on the mover device, and/or the counterforce exerted by a structure of the examination subject on the distal end portion of the medical object.

The providing of the correction preset may, for example, include a storing thereof on a computer-readable storage medium and/or a displaying thereof on a visualization unit and/or a transferring thereof to a provisioning unit. The provided correction preset may, for example, support an operator in controlling the mover device.

In a further embodiment of the proposed method for providing a correction preset, information relating to a physiological movement of the examination subject may also be received. In this case, the deviation may be identified taking into account the physiological movement.

In a further embodiment of the proposed method for providing a correction preset, a dataset containing an image and/or a model of the examination region may be received. The positioning information and/or the correction preset may also be determined based on the dataset.

In a further embodiment of the method for providing a correction preset, the correction preset may be determined by applying a trained function to input data. In this case, the input data may be based on the control preset. In addition, the input data may be based on the positioning information and/or the signal. Further, at least one parameter of the trained function may be based on a comparison of a training correction preset (e.g., a training correction instruction) with a comparison correction preset (e.g., a comparison correction instruction).

The trained function may have been trained by a machine learning method. For example, the trained function may be a neural network (e.g., a convolutional neural network (CNN)) or a network including a convolutional layer.

The trained function maps input data to output data. In this case, the output data may, for example, be dependent in addition on one or more parameters of the trained function. The one or more parameters of the trained function may be determined and/or adjusted by a training process. The determining and/or adjustment of the one or more parameters of the trained function may be based, for example, on a pairing consisting of training input data and associated training output data (e.g., comparison output data). The trained function is applied in order to generate training imaging data to the training input data. For example, the determining and/or adjustment may be based on a comparison of the training imaging data and the training output data (e.g., the comparison output data). Generally, a trainable function (e.g., a function having one or more parameters that have not yet been adjusted) is also referred to as a trained function.

Other terms for trained function are trained mapping rule, mapping rule with trained parameters, function with trained parameters, artificial-intelligence-based algorithm, and machine learning algorithm. An example of a trained function is an artificial neural network. The edge weights of the artificial neural network correspond to the parameters of the trained function. The term "neural net" may also be used instead of the term "neural network". For example, a trained function may also be a deep neural network or deep artificial neural network. Another example of a trained function is a "support vector machine"; further, other machine learning algorithms, for example, may also be used as a trained function.

The trained function may be trained, for example, by a backpropagation. First, training imaging data may be determined by applying the trained function to training input data. Next, a deviation between the training imaging data and the training output data (e.g., the comparison output data) may be determined by applying an error function to the training imaging data and the training output data (e.g., the comparison output data). Further, at least one parameter (e.g., a weighting) of the trained function (e.g., of the neural network) may be iteratively adjusted in respect of the at least one parameter of the trained function based on a gradient of the error function. The deviation between the training imaging data and the training output data (e.g., the comparison output data) may be minimized during the training of the trained function.

The trained function (e.g., the neural network) may include an input layer and an output layer. In this case, the input layer may be embodied to receive input data. Further, the output layer may be embodied for providing imaging data. In this case, the input layer and/or the output layer may each include a plurality of channels (e.g., neurons). The trained function may have an encoder-decoder architecture.

In one embodiment, at least one parameter of the trained function may be based on a comparison of the training correction preset with the comparison correction preset. In this case, the training correction preset and/or the comparison correction preset may be provided as part of a proposed computer-implemented method for providing a trained function. The method is explained in the further course of the description. For example, the trained function may be provided by an embodiment of the proposed computer-implemented method for providing a trained function.

The present embodiments relate, in a fourth aspect, to a method (e.g., a computer-implemented method) for providing a trained function. In a first act, a training correction preset is received. In this case, the training control preset includes a preset specified for a first movement of at least a predefined section of a medical object. Further, the medical object may be halted and/or moved by a mover device by transmission of a force in accordance with the training control preset. Moreover, the predefined section of the medical object may be arranged in a training examination subject. In a second act, training positioning information relating to a spatial positioning of the predefined section of the medical object is received. Alternatively or in addition, a training signal containing information is received relating to a counterforce that acts in the opposite direction to the force. In a third act, a training deviation between a movement state of the predefined section of the medical object and the first movement is identified based on the training positioning information and/or the training signal. In a fourth act, a comparison correction preset is determined. In this case, the determining of the comparison correction preset includes a simulation of movement trajectories of the predefined section of the medical object. Further, the movement trajectory that minimizes the training deviation is identified by a comparison. The comparison correction preset further includes a preset specified for a corrective movement of the predefined section along the identified movement trajectory. In a fifth act, a training correction preset is determined by applying the trained function to input data. In this case, the input data is based on the training control preset. The input data is based in addition on the training control preset and/or the training signal. In a sixth act, at least one parameter of the trained function is adjusted based on a comparison of the training correction preset with the comparison correction preset. The trained function is provided in a seventh act.

The receiving of the training control preset and/or the training positioning information and/or the training signal may, for example, include an acquisition thereof and/or a readout thereof from a computer-readable data storage medium and/or a receiving thereof from a computer-readable data storage medium and/or a receiving thereof from a data storage unit (e.g., a database).

In this case, the training control preset may be provided by an input unit for acquiring an input by an operator. Further, the training positioning information may be provided by an acquisition unit (e.g., a medical imaging device). In this case, the acquisition unit may be embodied for acquiring a spatial positioning of the predefined section. The training signal may be provided by a sensor unit for detecting the counterforce. In this case, the sensor unit may be embodied to detect the counterforce exerted by the medical object on the mover device and/or the counterforce exerted by a structure of the examination subject on the distal end portion of the medical object. Further, the training control preset and/or the training signal and/or the training positioning information may be simulated.

The training control preset may, for example, possess all the characteristics of the control preset that have been described in relation to the device for moving a medical object and/or to the method for providing a correction preset, and vice versa.

The training examination subject may be a human and/or animal patient and/or a vessel phantom. Further, the training examination subject may be different from or the same as the examination subject that has been described in relation to the device for moving a medical object and/or to the method for providing a correction preset. For example, the training examination subject may include a hollow organ in which the predefined section of the medical object may be arranged. Further, the training positioning information and/or the training signal and/or the training deviation may each possess the characteristics of the positioning information and/or of the signal and/or of the deviation that have been described in relation to the device for moving a medical object and/or to the method for providing a correction preset, and vice versa. For example, the training deviation may be identified analogously to the deviation that has been described in relation to the device for moving a medical object and/or to the method for providing a correction preset.

The determining of the comparison correction preset may include a simulation of, for example, different movement trajectories of the predefined section of the medical object. In this case, the simulation of the movement trajectories may be based on a biophysical model of the training examination subject (e.g., a centerline model and/or a volume model of the hollow organ), and/or a physical model of the medical object. Further, the simulation of the movement trajectories may be based on a material parameter and/or an operating parameter of the medical object and/or a physiological parameter and/or a tissue parameter of the training examination subject. In one embodiment, the simulated movement trajectories include a virtual translation and/or rotation of the predefined section at least partially counter to a first movement direction of the first movement. In one embodiment, the comparison of the movement trajectories enables that movement trajectory to be identified, which minimizes the training deviation. In this case, the comparison of the movement trajectories may be based, for example, on a sorting and/or placement technique. Further, a particular anatomical feature of the examination subject (e.g., a pathology that is present) may be taken into account in the comparison of the movement trajectories.

Further, the comparison correction preset may include a preset specified for a corrective movement of the predefined section along the identified movement trajectory. For example, the comparison correction preset may include at least one command for a control (e.g., incremental control) of the mover device. Moreover, the comparison correction preset may include at least one command (e.g., a temporal sequence of commands) for specifying the corrective movement of the predefined section of the medical object along the identified movement trajectory.

The training correction preset may be generated by applying the trained function to the input data. In this case, the input data may be based on the training control preset. The input data may be based in addition on the training positioning information and/or the training signal. The comparison between the training correction preset and the comparison correction preset further enables the at least one parameter of the trained function to be adjusted. In this case, the at least one parameter of the trained function may be adjusted such that a deviation between the training correction preset and the comparison correction preset is minimized. The adjustment of the at least one parameter of the trained function may, for example, include an optimization (e.g., a minimization) of a cost value of a cost function. The cost function characterizes the deviation between the training correction preset and the comparison correction preset. For example, the adjustment of the at least one parameter of the trained function may include a regression of the cost value of the cost function.

The providing of the trained function may, for example, include a storing thereof on a computer-readable storage medium and/or a transferring thereof to a provisioning unit. In one embodiment, this enables a trained function that may be used in an embodiment of the proposed method for providing a correction preset to be provided.

The present embodiments may further relate to a training unit that includes a training computing unit, a training memory unit, and a training interface. In this case, the training unit may be embodied to implement an embodiment of the proposed method for providing a trained function in that the components of the training unit are embodied to perform the individual method acts.

The advantages of the proposed training unit substantially correspond to the advantages of the proposed method for providing a trained function. Features, advantages, or alternative embodiments mentioned in this context may equally be applied also to the other claimed subject matters, and vice versa.

The present embodiments relate, in a fifth aspect, to a computer program product including a computer program that may be loaded directly into a memory of a provisioning unit and having program sections for performing all the acts of the computer-implemented method for providing a correction preset and/or one of its aspects when the program sections are executed by the provisioning unit; alternatively or additional, the computer program may be loaded directly into a training memory of a training unit and has program sections for performing all the acts of the proposed method for providing a trained function and/or one of its aspects when the program sections are executed by the training unit.

The present embodiments may further relate to a computer-readable storage medium on which there are stored program sections that may be read and executed by a provisioning unit for the purpose of performing all the acts of the method for providing a correction preset and/or one of its aspects when the program sections are executed by the provisioning unit; alternatively or additionally, program sections that may be read and executed by a training unit for the purpose of performing all the acts of the method for providing a trained function and/or one of its aspects when the program sections are executed by the training unit may be stored on the computer-readable storage medium.

The present embodiments may further relate to a computer program or computer-readable storage medium including a trained function provided by a proposed computer-implemented method or one of its aspects.

An implementation to a large extent in the form of software has the advantage that provisioning units and/or training units already used previously may also be easily upgraded using a software update in order to operate in the manner according to the present embodiments. In addition to the computer program, such a computer program product may, where necessary, include additional constituent parts such as, for example, a set of documentation and/or additional components, as well as hardware components, such as, for example, hardware keys (e.g., dongles, etc.) to enable use of the software.

BRIEF DESCRIPTION OF THE DRAWINGS

The same reference characters are used for like features in different figures, in which.

DETAILED DESCRIPTION

Figure 1:
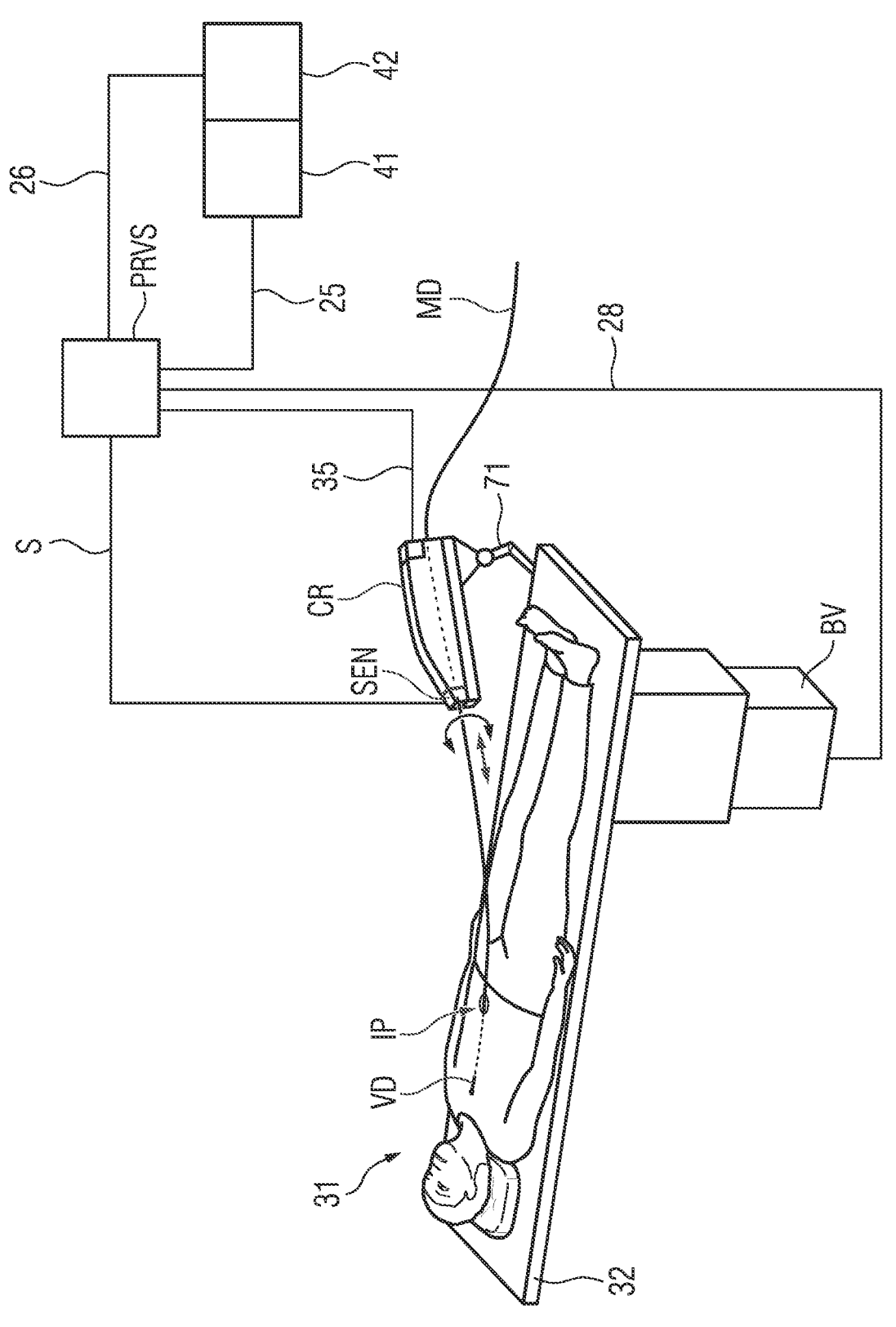
FIG. 1 shows a schematic view of one embodiment of a device for moving a medical object.

FIG. 1 shows a schematic view of one embodiment of a device for moving a medical object. In this case, the device may include a mover device CR for robotically moving a medical object MD. The device may further include a provisioning unit PRVS.

The mover device CR may be embodied, for example, as a catheter robot, for example, to allow remote manipulation of the medical object MD. The medical object MD may be embodied as, for example, an elongate, surgical, and/or diagnostic instrument. For example, the medical object MD may be flexible and/or mechanically deformable and/or rigid, at least in sections. The medical object MD may be embodied, for example, as a catheter and/or an endoscope and/or a guide wire. Further, the medical object MD may have a predefined section VD. In this case, the predefined section VD may describe, for example, a tip and/or, for example, a distal section of the medical object MD. The predefined section VD may further include a marker structure. In an operating state of the device, the predefined section VD of the medical object MD may be arranged at least partially in an examination region of an examination subject 31 (e.g., in a hollow organ). In the operating state of the device, the medical object MD may, for example, be introduced via an introducer sheath at an insertion point or port IP into the examination subject 31 disposed on the patient support and positioning device 32 (e.g., into the hollow organ of the examination subject 31). In this case, the hollow organ may, for example, contain a vessel section in which the predefined section VD is at least partially arranged in the operating state of the device. Further, the patient support and positioning device 32 may be at least partially movable. For this purpose, the patient support and positioning device 32 may include a mover unit BV that is controllable by a signal 28 from the provisioning unit PRVS.

The mover device CR may further be fixedly secured to the patient support and positioning device 32 by a securing element 71 (e.g., a stand and/or a robotic arm), for example, so as to be movable. The mover device CR may be embodied to halt and/or move the medical object MD by transmission of a force. For example, the mover device CR may be embodied to move the medical object MD arranged therein translationally at least along a longitudinal extension direction of the medical object MD. The mover device CR may be further embodied to rotate the medical object MD around the longitudinal extension direction. Alternatively or in addition, the mover device CR may be embodied to control a movement of at least a part of the medical object MD (e.g., a distal section and/or a tip of the medical object MD, such as the predefined section VD). In addition, the mover device CR may be embodied to deform the predefined section VD of the medical object MD in a defined manner (e.g., via a Bowden cable inside the medical object MD).

The device may include an input unit 42 (e.g., a keyboard) and/or a visualization unit 41 (e.g., a monitor and/or a display). The input unit 42 may be integrated into the visualization unit 41 (e.g., in the case of a capacitive and/or resistive input display). The device (e.g., the provisioning unit PRVS) may be embodied to receive a control preset. The control preset may, for example, be acquired by an input by an operator on the input unit 42. For this, the input unit 42 may, for example, send a signal 26 to the provisioning unit PRVS. In one embodiment, the control preset may specify a first movement for the predefined section VD of the medical object MD. The mover device CR may be further embodied to move the medical object MD along a first movement direction. The device (e.g., the provisioning unit PRVS) may be further embodied to identify a deviation between a movement state (e.g., a current movement state) of the predefined section VD of the medical object MD and the first movement. The device may be further embodied to determine a correction preset for minimizing the deviation. The provisioning unit PRVS may be further embodied to provide the correction preset to the mover device CR using the signal 35. The mover device CR may in this case be embodied to move the medical object MD at least partially counter to the first movement direction in accordance with the correction preset.

The mover device CR may be embodied to move the medical object MD along the first movement direction in accordance with the control preset such that the predefined section VD of the medical object MD executes a feed-forward movement and/or rotational movement. The mover device CR may also be embodied to move the medical object MD at least partially counter to the first movement direction in accordance with the correction preset such that the predefined section VD of the medical object MD executes a withdrawal movement and/or counterrotational movement.

The device may be further embodied to receive information relating to a physiological movement of the examination subject 31. In this case, the device may be embodied to identify the deviation taking into account the physiological movement.

The device may be further embodied to receive a signal S from a sensor unit SEN. In this case, the sensor unit SEN may be at least partially integrated into the mover device CR. The sensor unit may be further embodied to detect a counterforce exerted by the medical object MD on the mover device CR and acting in the opposite direction to the force. The sensor unit SEN may be further embodied to provide the signal S to the provisioning unit PRVS as a function of the counterforce. The device may be further embodied to identify the deviation based on the signal S.

Alternatively, the sensor unit SEN may be arranged at a distal end portion (e.g., the predefined section) of the medical object MD (not shown here). In this case, the sensor unit SEN may be embodied to detect the counterforce exerted by a structure of the examination subject 31 on the distal end portion of the medical object MD.

The device may be further embodied to receive a dataset containing information relating to a spatial positioning of the predefined section VD of the medical object MD. The device may be further embodied to identify the deviation using a comparison of the positioning information with the control preset.

The visualization unit 41 may be embodied to display information and/or graphical representations of information of the device and/or of the medical C-arm X-ray device 37 and/or of the provisioning unit PRVS and/or of other components. For this purpose, the provisioning unit PRVS may, for example, send a signal 25 to the visualization unit 41.

Figure 2:
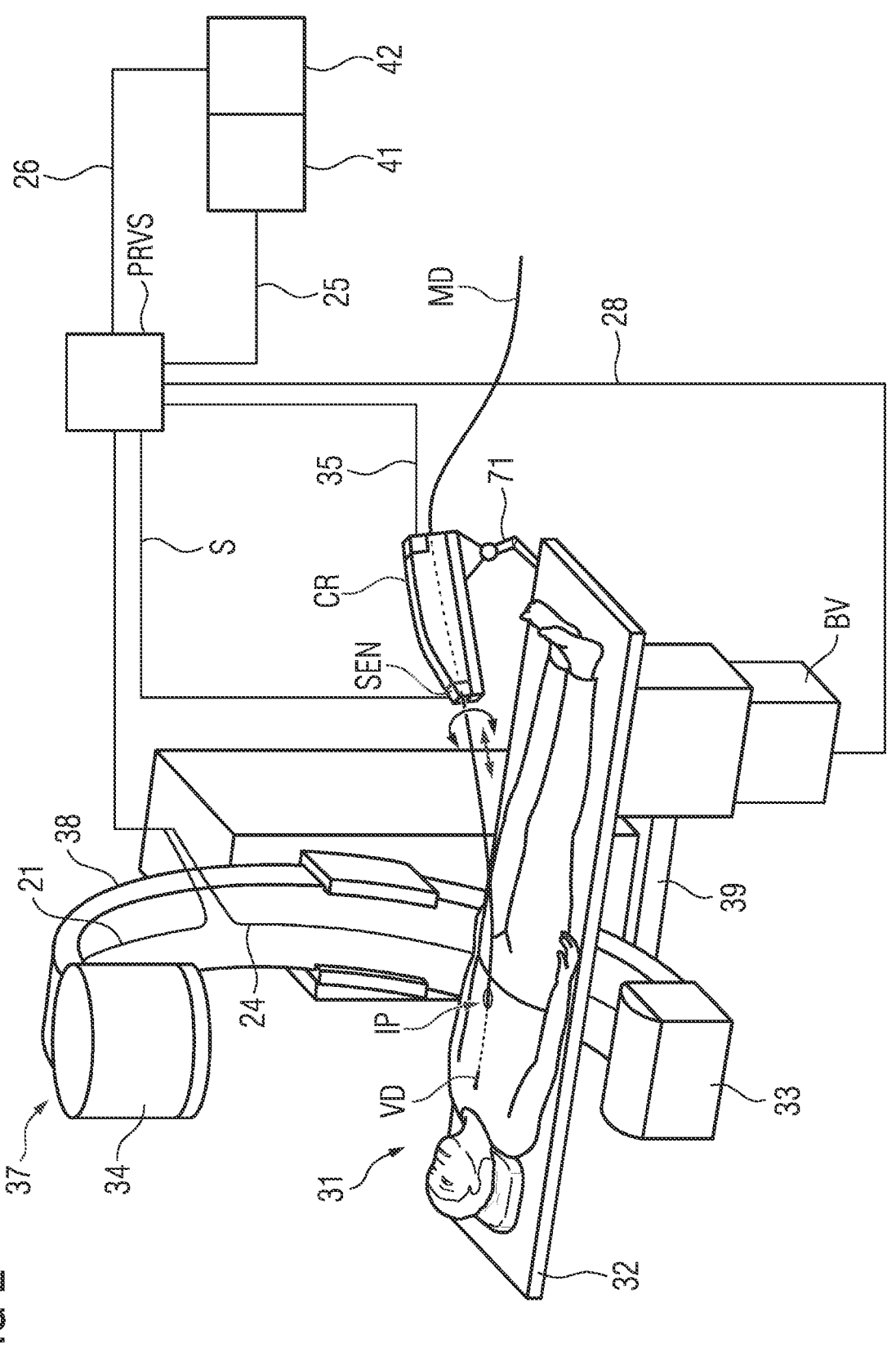
FIG. 2 shows a schematic view of one embodiment of a system.

FIG. 2 shows one embodiment of a system in a schematic view. The system includes a device for moving a medical object MD of one or more of the present embodiments and an acquisition unit. Further, the acquisition unit may be embodied as a medical imaging device (e.g., as a medical C-arm X-ray device 37). The C-arm X-ray device 37 may be embodied to acquire the dataset containing an image of the examination region (e.g., of the predefined section VD of the medical object MD arranged therein in the operating state of the device), and to provide the dataset to the device (e.g., to the provisioning unit PRVS). In this case, the device may be further embodied to determine the positioning information and/or the correction preset on the basis of the dataset.

The medical imaging device in the exemplary embodiment in the form of a medical C-arm X-ray device 37 may include a detector 34 (e.g., an X-ray detector) and an X-ray source 33. In order to acquire the dataset, the arm 38 of the medical C-arm X-ray device 37 may be mounted so as to be movable around one or more axes. Further, the medical C-arm X-ray device 37 may include a further mover unit 39 (e.g., a wheel system and/or rail system and/or a robotic arm) that enables the medical C-arm X-ray device 37 to execute movements in space. The detector 34 and the X-ray source 34 may be movably secured to a common C-arm 38 in a defined arrangement.

The provisioning unit PRVS may also be embodied to control a positioning of the medical C-arm X-ray device 37 relative to the examination subject 31 such that the pre-defined section VD of the medical object MD is imaged in the dataset acquired by the medical C-arm X-ray device 37. The positioning of the medical C-arm X-ray device 37 relative to the examination subject 31 may, for example, include a positioning of the defined arrangement of X-ray source 33 and detector 34 (e.g., of the C-arm 38) around one or more spatial axes.

In order to acquire the dataset of the examination region 31, the provisioning unit PRVS may send a signal 24 to the X-ray source 33. The X-ray source 33 may thereupon transmit an X-ray beam (e.g., a cone beam and/or fan beam and/or parallel beam). When the X-ray beam is incident on a surface of the detector 34 following an interaction with the examination region to be imaged of the examination subject 31, the detector 34 may send a signal 21 to the provisioning unit PRVS. The provisioning unit PRVS may receive the dataset, for example, based on the signal 21.

Figure 3:
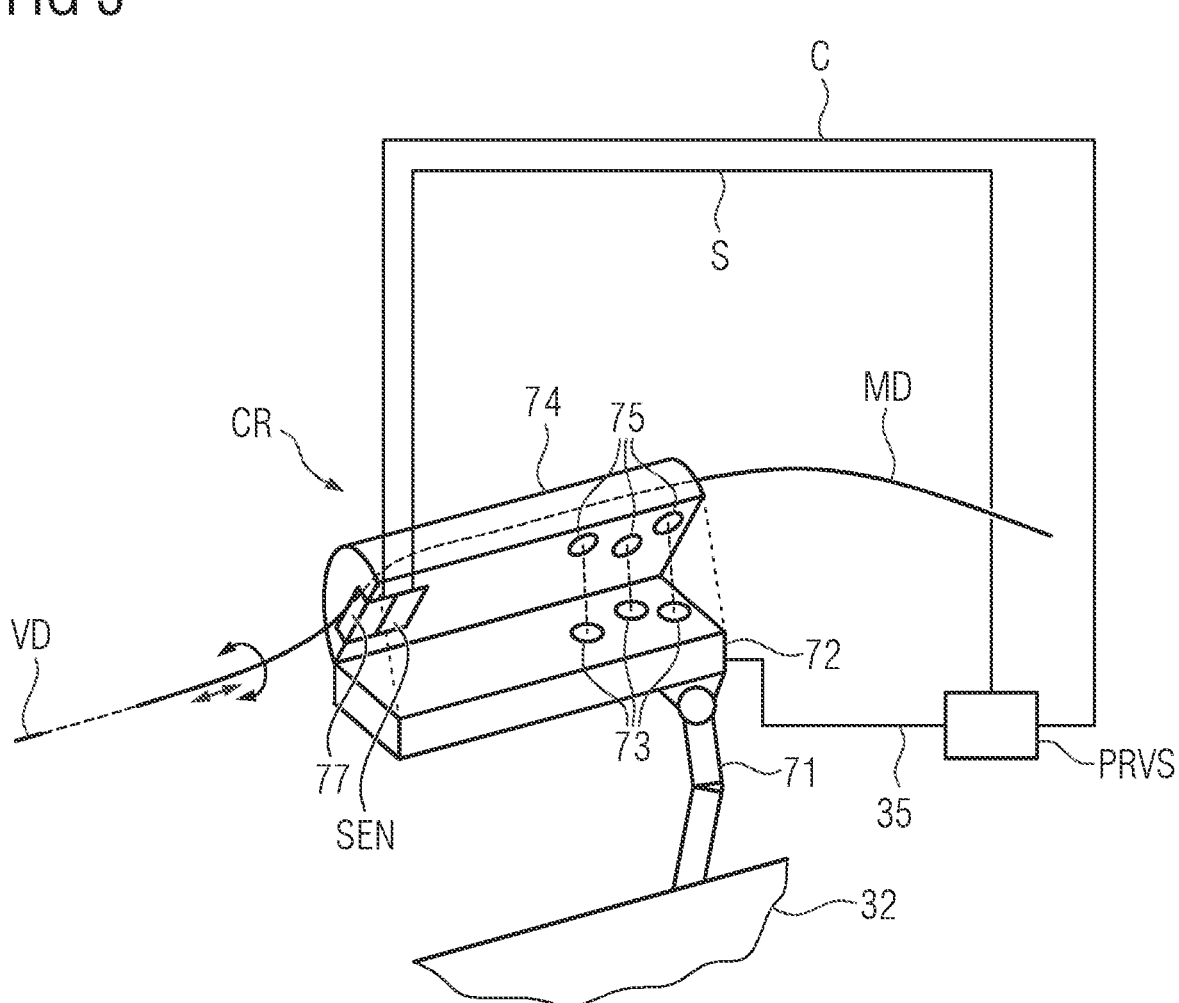
FIG. 3 shows a schematic view of one embodiment of a mover device.

FIG. 3 shows a schematic view of the mover device CR for robotically moving the medical object MD. The mover device CR may include a securing element 71 (e.g., movable and/or maneuverable securing element). The mover device CR may further include a cassette element 74 that is embodied to accommodate at least a part of the medical object MD. The mover device CR may further include a mover element 72 that is fixedly mounted to the securing element 71 (e.g., a stand and/or a robotic arm). Further, the securing element 71 may be embodied to secure the mover element 72 to the patient support and positioning device 32 (e.g., so as to be movable). Further, the mover element 72 may include at least one (e.g., three) actuator element(s) 73 (e.g., an electric motor). The provisioning unit PRVS is embodied to control the at least one actuator element 73. In one embodiment, the cassette element 74 may be couplable (e.g., mechanically and/or electromagnetically and/or pneumatically) to the mover element 72 (e.g., to the at least one actuator element 73). In this case, the cassette element 74 may further include at least one transmission element 75 that is movable owing to the coupling between the cassette element 74 and the mover element 72 (e.g., the at least one actuator element 73). For example, the at least one transmission element 75 may be movably coupled to the at least one actuator element 73. The transmission element 75 may be further embodied to transmit a movement of the actuator element 73 to the medical object MD such that the medical object MD is moved along a longitudinal extension direction of the medical object MD and/or that the medical object MD is rotated around the longitudinal extension direction. The at least one transmission element 75 may include, for example, a roller and/or drum and/or shield and/or shearing plate.

In one embodiment, the mover element 72 may include a plurality of actuator elements 73 (e.g., independently controllable actuator elements 73). Further, the cassette element 74 may include a plurality of transmission elements 75 (e.g., at least one movably coupled transmission element 75 for each of the actuator elements 73). This may facilitate a movement (e.g., independent and/or simultaneous movement) of the medical object MD along different degrees of freedom of movement.

Further, the mover device CR (e.g., the at least one actuator element 73) may be controllable by the signal 35 from the provisioning unit PRVS. By this, the movement of the medical object MD may be controlled (e.g., indirectly) by the provisioning unit PRVS. Moreover, an orientation and/or position of the mover device CR relative to the examination subject 31 may be adjustable by a movement of the securing element 71. The mover device CR may be embodied to receive the control preset.

In addition, the mover device CR may include a sensor unit 77 that is embodied to detect a relative movement of the medical object MD relative to the mover device CR. In this case, the sensor unit 77 may include, for example, an encoder (e.g., a wheel encoder and/or a roller encoder) and/or an optical sensor (e.g., a barcode scanner and/or a laser scanner and/or a camera) and/or an electromagnetic sensor. For example, the sensor unit 77 may be arranged at least partially integrated into the mover element 72 (e.g., the at least one actuator element 73) and/or into the cassette element 74 (e.g., the at least one transmission element 75). The sensor unit 77 may be embodied, for example, to detect the relative movement of the medical object MD by detecting the medical object MD relative to the mover device CR. Alternatively or in addition, the sensor unit 77 may be embodied to detect a movement and/or change in position of components of the mover device CR. The components are movably coupled to the medical object MD (e.g., the at least one actuator element 73 and/or the at least one transmission element 74).

The device (e.g., the provisioning unit PRVS) may be embodied to receive a signal C from the sensor unit 77 (e.g., containing information relating to the detected relative movement of the medical object MD in relation to the mover device CR).

Figure 4:
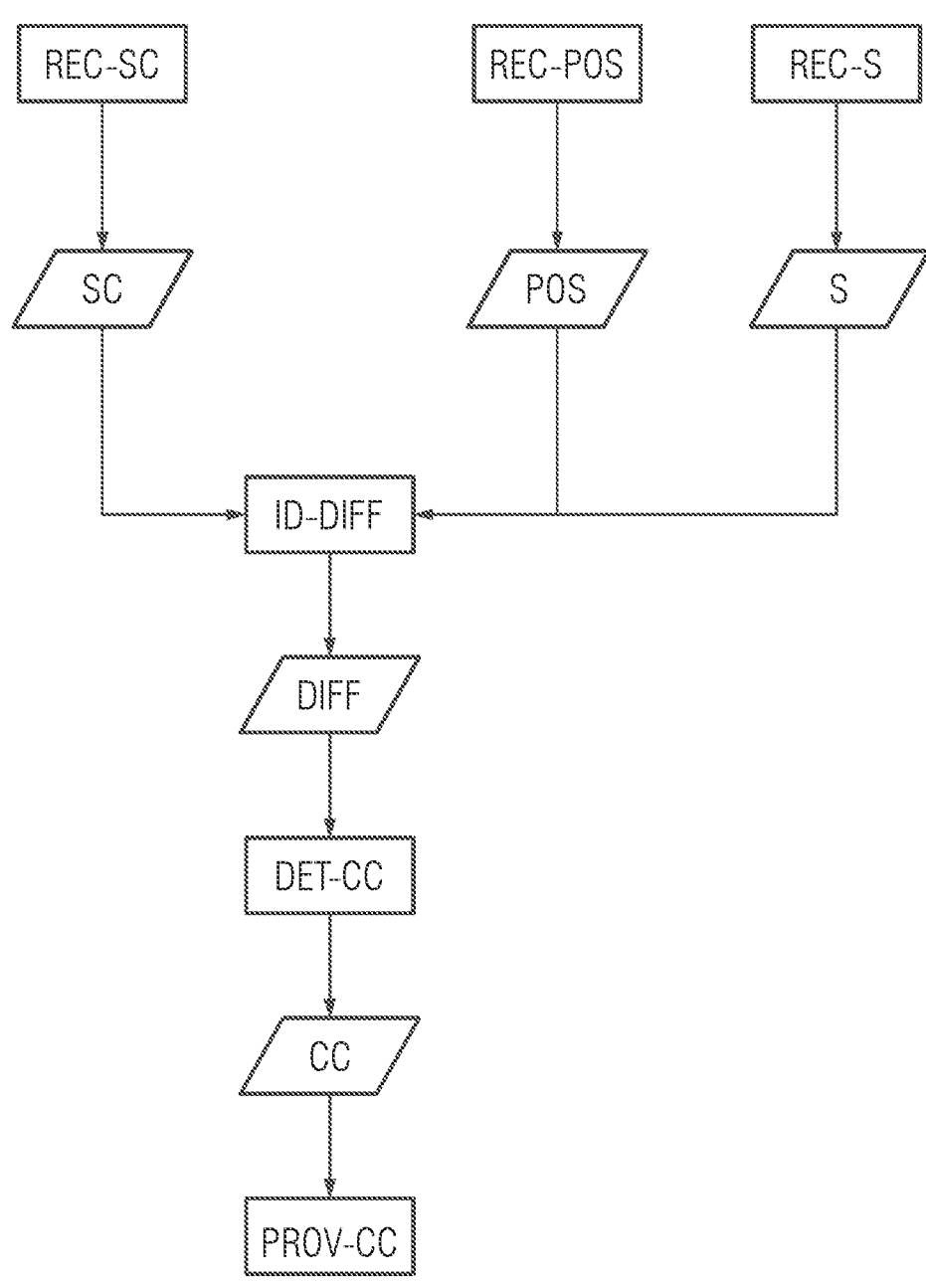
FIGS. 4 to 6 show schematic views of different embodiments of a method for providing a correction preset.

FIG. 4 shows a schematic illustrating an embodiment of a method for providing a correction preset PROV-CC. In this case, a movement of the medical object MD may have taken place along a first movement direction using the mover device CR prior to the start of the method. In this case, the mover device CR may be embodied to halt and/or move the medical object MD at least partially arranged in the mover device CR by transmitting a force in accordance with a control preset SC. Further, at least the predefined section VD of the medical object MD may be arranged in the examination subject 31. In a first act, the control preset SC may be received REC-SC. In this case, the control preset SC may have specified the first movement for the predefined section VD of the medical object MD prior to the start of the method. In a second act, the positioning information POS relating to the spatial positioning of the predefined section VD of the medical object MD may be received REC-POS. Alternatively or in addition, the signal S containing information relating to a counterforce may be received REC-S in the second act. The counterforce acts in the opposite direction to the force. In a third act, the deviation DIFF between the movement state of the predefined section VD of the medical object MD and the first movement may be identified ID-DIFF based on the positioning information POS and/or of the signal S. In a fourth act, the correction preset CC containing information for minimizing the deviation DIFF may be determined DET-CC. In a fifth act, the correction preset CC may be provided PROV-CC.

In one embodiment, information relating to a physiological movement of the examination subject 31 may be received in addition. The deviation DIFF may be identified ID-DIFF in this case taking into account the physiological movement.

Figure 5:
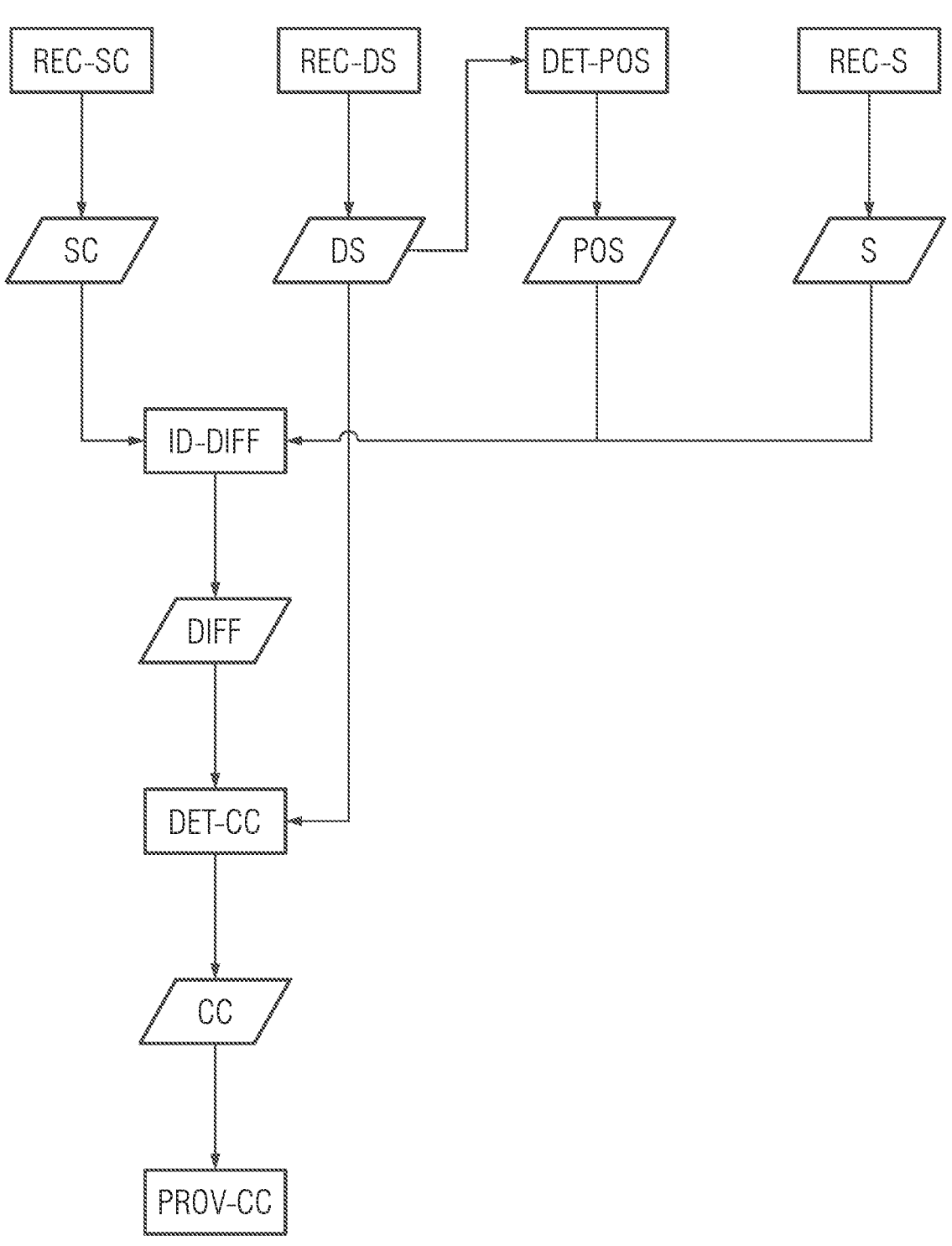

FIG. 5 shows a schematic view of a further embodiment of a method for providing a correction preset PROV-CC. In this case, a dataset DS containing an image and/or a model of the examination region may be received REC-DS. Further, the positioning information POS may be determined DET-POS based on the dataset DS. Alternatively or in addition, the correction preset CC may be determined DET-CC based on the dataset DS.

Figure 6:
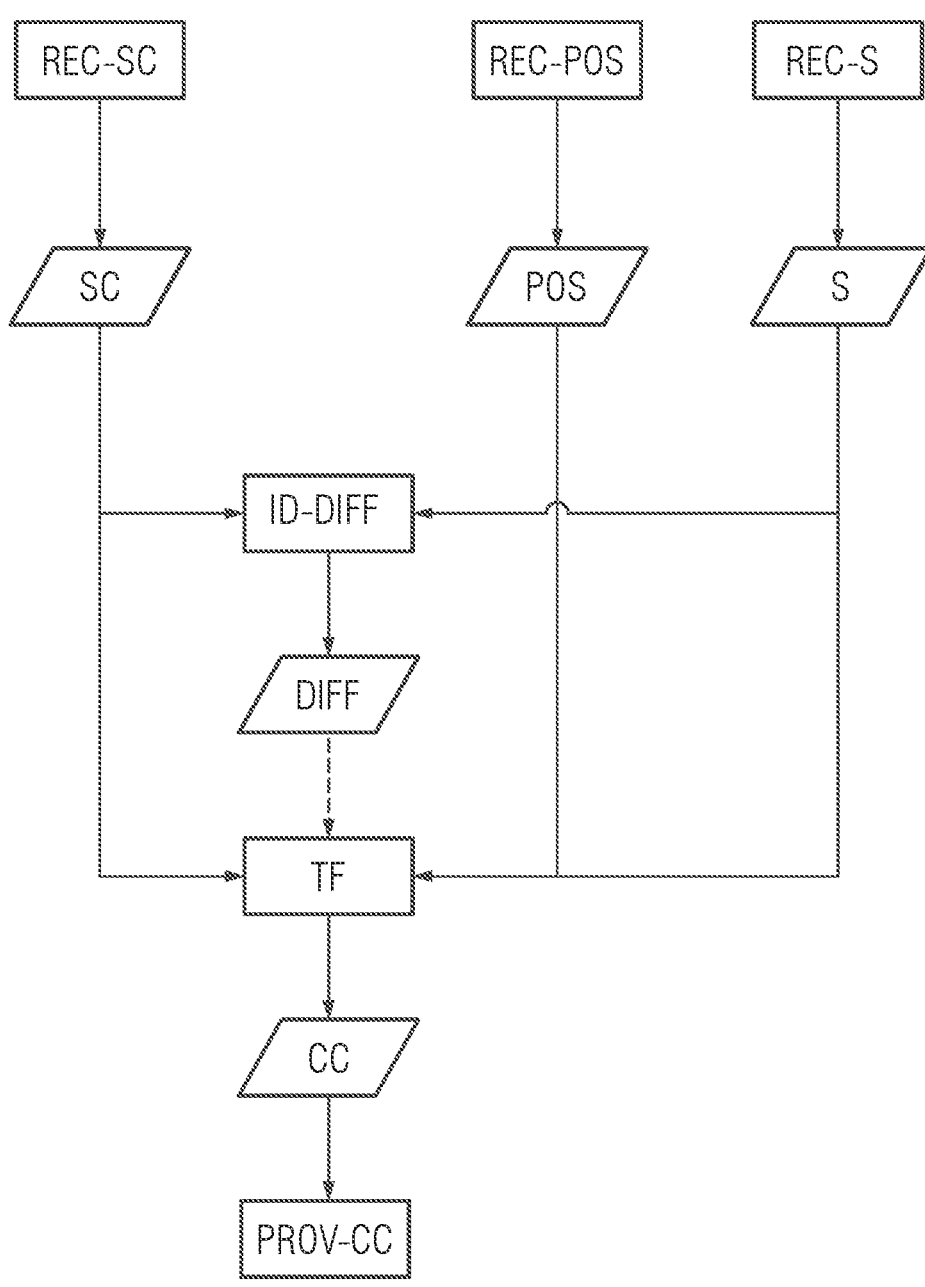

FIG. 6 shows a schematic view of a further embodiment of a method for providing a correction preset PROV-CC. In this case, the correction preset DET-CC may be determined by applying a trained function TF to input data. The input data may be based on the control preset SC. The input data may also be based on the positioning information POS and/or the signal S. Further, at least one parameter of the trained function TF may be based on a comparison of a training correction preset with a comparison correction preset.

Figure 7:
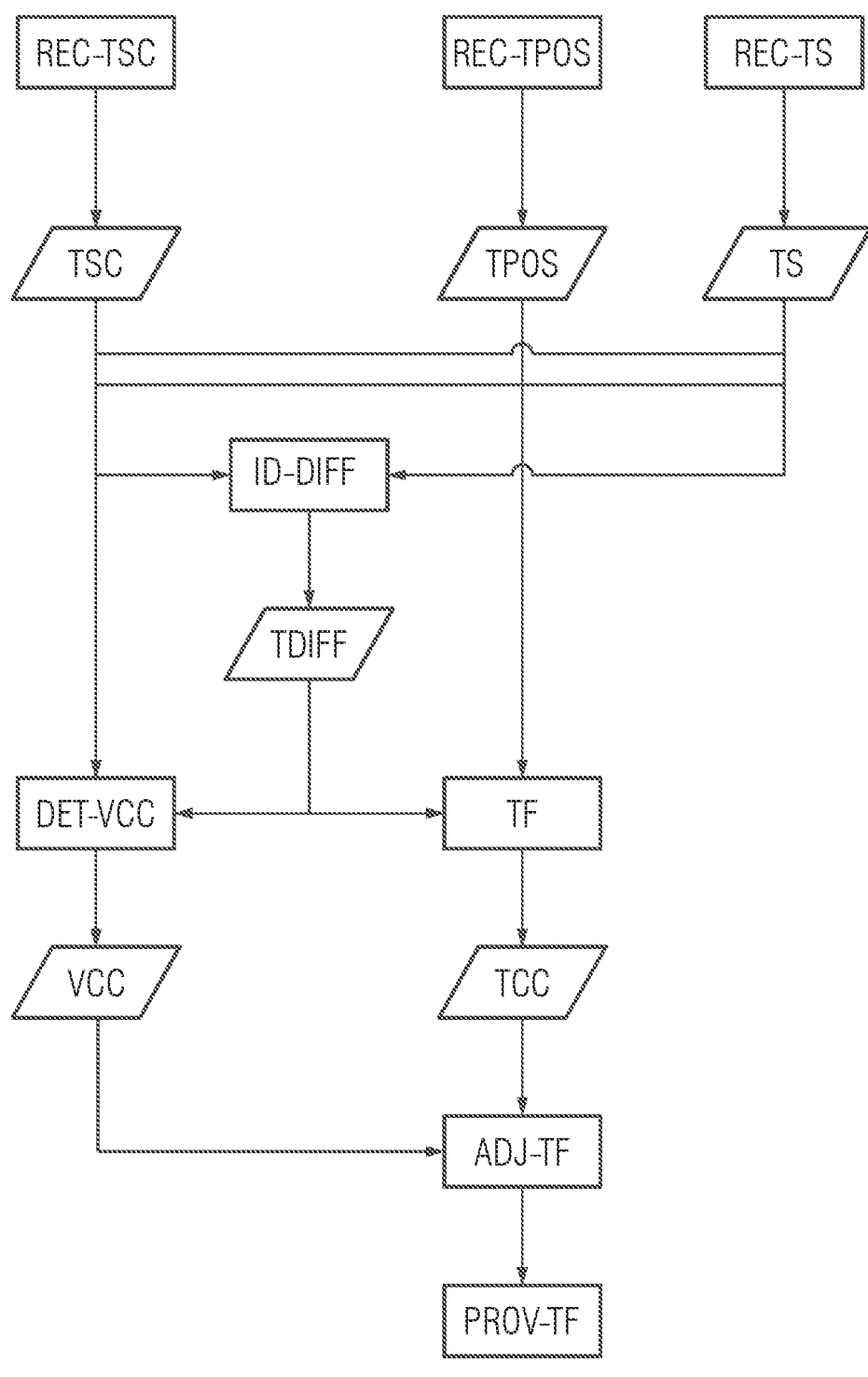
FIG. 7 shows a schematic view of one embodiment of a method for providing a trained function.

FIG. 7 shows an embodiment of a method for providing a trained function PROV-TF in a schematic view. In a first act, a training control preset TSC may be received REC-TSC. In this case, the training control preset TSC may include a preset specified for a first movement of at least the predefined section VD of the medical object MD. Further, in a second act, training positioning information TPOS for spatially positioning the predefined section VD of the medical object MD may be received REC-TPOS. Alternatively or in addition, a training signal TS containing information relating to a counterforce acting in the opposite direction to the force may be received REC-TS. In a third act, a training deviation TDIFF between the movement state of the predefined section VD of the medical object MD and the first movement may be identified ID-TDIFF based on the training positioning information TPOS and/or the training signal TS. In a fourth act, a comparison correction preset VCC may be determined DET-VCC. In this case, the determining of the comparison correction preset DET-VCC may include a simulation of movement trajectories of the predefined section VD of the medical object MD. Further, the movement trajectory that minimizes the training deviation TDIFF may be identified using a comparison. The comparison correction preset VCC may also include a preset specified for a corrective movement of the predefined section VD along the identified movement trajectory. In a fifth act, a training correction preset TCC may be determined by applying the trained function TF to input data. In this case, the input data of the trained function TF may be based on the training control preset TCC. The input data may also be based on the training positioning information TPOS and/or the training signal TS. In a sixth act, at least one parameter of the trained function TF may be adjusted ADJ-TF based on a comparison of the training correction preset TCC with the comparison correction preset VCC. After this, the trained function TF may be provided PROV-TF in a seventh act.

Figure 8:
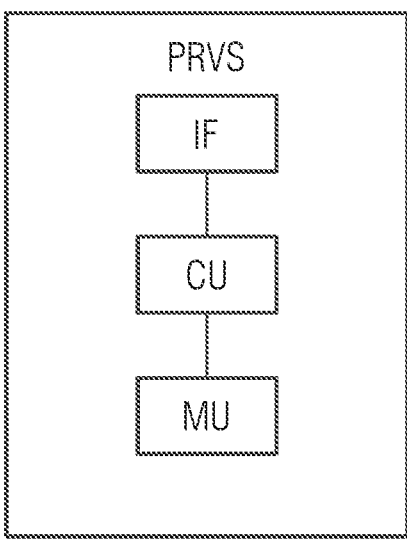
FIG. 8 shows a schematic view of one embodiment of a provisioning unit.

FIG. 8 shows a proposed provisioning unit PRVS in a schematic view. In this case, the provisioning unit PRVS may include an interface IF, a computing unit CU, and a memory unit MU. The provisioning unit PRVS may be embodied to implement a method for providing a correction preset PROV-CC and corresponding aspects in that the interface IF, the computing unit CU, and the memory unit MU are embodied to perform the corresponding method acts.

Figure 9:
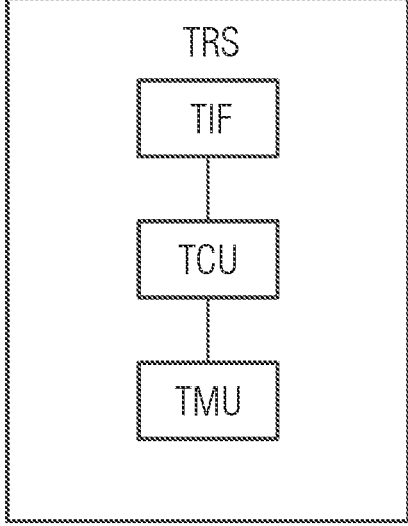
FIG. 9 shows a schematic view of one embodiment of a training unit.

FIG. 9 shows a schematic view of one embodiment of a training unit TRS. The training unit TRS may include a training interface TIF, a training memory unit TMU, and a training computing unit TCU. The training unit TRS may be embodied to implement a method for providing a trained function PROV-TF and corresponding aspects in that the training interface TIF, the training memory unit TMU, and the training computing unit TCU are embodied to perform the corresponding method acts.

The provisioning unit PRVS and/or the training unit TRS may be, for example, a computer, a microcontroller, or an integrated circuit. Alternatively, the provisioning unit PRVS and/or the training unit TRS may be a real or virtual network of interconnected computers (e.g., a technical term for a real computer network is "cluster", a technical term for a virtual computer network is "cloud"). The provisioning unit PRVS and/or the training unit TRS may also be embodied as a virtual system that is implemented on a real computer or a real or virtual network of interconnected computers (e.g., "virtualization").

An interface IF and/or a training interface TIF may be a hardware or software interface (e.g., PCI bus, USB or Firewire). A computing unit CU and/or a training computing unit TCU may include hardware elements or software elements (e.g., a microprocessor or a device known as a "Field Programmable Gate Array" (FPGA). A memory unit MU and/or a training memory unit TMU may be realized as a volatile working memory known as Random Access Memory (RAM) or as a nonvolatile mass storage device (e.g., hard disk drive, USB stick, SD card, solid state disk).

The interface IF and/or the training interface TIF may, for example, include a plurality of subsidiary interfaces that perform different acts of the respective methods. In other words, the interface IF and/or the training interface TIF may also be regarded as a plurality of interfaces IF or, as the case may be, as a plurality of training interfaces TIF. The computing unit CU and/or the training computing unit TCU may, for example, include a plurality of subsidiary computing units that perform different acts of the respective methods. In other words, the computing unit CU and/or the training computing unit TCU may also be understood as a plurality of computing units CU or as a plurality of training computing units TCU.

The schematic illustrations contained in the described figures do not reflect a scale or proportions of any kind.

In conclusion, the methods described in detail in the foregoing, as well as the illustrated devices, are simply exemplary embodiments that may be modified in the most diverse ways by the person skilled in the art without leaving the scope of the invention. Further, the use of the indefinite articles "a" or "an" does not exclude the possibility that the features in question may also be present more than once. Similarly, the terms "unit" and "element" do not rule out the possibility that the components in question consist of a plurality of cooperating subcomponents that, if necessary, may also be distributed in space.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A device for moving a medical object, the device comprising:

a mover device for robotically moving the medical object, wherein at least a predefined section of the medical object is arranged in an examination subject in an operating state of the device, wherein the device is configured to receive a control instruction, the control instruction specifying a first movement for the predefined section of the medical object, and wherein the mover device is configured to:

move the medical object along a first movement direction in accordance with the control instruction;

identify a deviation between a movement state of the predefined section of the medical object and the first movement, the movement state of the predefined section of the medical object including a movement speed of the predefined section of the medical object;

determine a correction instruction, such that the deviation is minimized; and move the medical object at least partially counter to the first movement direction in accordance with the correction instruction.

2. The device of claim 1, wherein the mover device is further configured to hold, move, or hold and move the medical object by transmitting a force, and wherein the device is further configured to:

receive a signal from a sensor unit, the sensor unit being configured to:

detect a counterforce acting in an opposite direction to the force;

provide the signal as a function of the counterforce; and identify the deviation based on the signal.

3. The device of claim 2, wherein the sensor unit is at least partially integrated into the mover device, and wherein the sensor unit is further configured to detect the counterforce exerted by the medical object on the mover device.

4. The device of claim 2, wherein the sensor unit is arranged at a distal end portion of the medical object, and wherein the sensor unit is further configured to detect the counterforce exerted by a structure of the examination subject on a distal end portion of the medical object.

5. The device of claim 1, wherein the mover device is further configured to:

move the medical object along the first movement direction in accordance with the control instruction such that the predefined section of the medical object executes a feed-forward movement, a rotational movement, or a feed-forward and rotational movement; and move the medical object at least partially counter to the first movement direction in accordance with the correction instruction such that the predefined section of the medical object executes a withdrawal movement, a counterrotational movement, or a withdrawal and counterrotational movement.

6. The device of claim 1, wherein the device is further configured to:

receive information relating to a physiological movement of the examination subject; and identify the deviation taking into account the physiological movement.

7. The device of claim 1, wherein the device is further configured to:

receive, determine, or receive and determine positioning information relating to a spatial positioning of the predefined section of the medical object; and identify the deviation using a comparison of the positioning information with the control instruction.

8. The device of claim 7, wherein the device is further configured to:

receive a dataset containing an image, a model, or the image and the model of the examination region; and determine the positioning information, the correction instruction, or the positioning information and the correction instruction based on the dataset.

9. The device of claim 8, further comprising:

an acquisition unit, wherein the acquisition unit is configured to acquire the positioning information and provide the positioning information to the device.

10. The device of claim 9, wherein the acquisition unit is configured as a medical imaging device that is configured to acquire the dataset and provide the dataset to the mover device.

11. The device of claim 1, wherein the movement state of the predefined section of the medical object further includes a movement direction of the predefined section of the medical object.

12. A method for providing a correction instruction, the method comprising:

receiving a control instruction, wherein a mover device is configured to hold, move, or hold and move a medical object at least partially arranged in the mover device by transmitting a force in accordance with the control instruction, at least a predefined section of the medical object being arranged in an examination subject, and wherein the control instruction specifies a first movement for the predefined section of the medical object along a first movement direction using the mover device;

receiving, determining, or receiving and determining positioning information relating to a spatial positioning of the predefined section of the medical object, receiving a signal containing information relating to a counterforce acting in an opposite direction to the force, or a combination thereof;

identifying a deviation between a movement state of the predefined section of the medical object and the first movement based on the positioning information, the signal, or the positioning information and the signal, the movement state of the predefined section of the medical object including a movement speed of the predefined section of the medical object;

determining the correction instruction containing information for minimizing the deviation; and providing the correction instruction.

13. The method of claim 12, further comprising receiving information relating to a physiological movement of the examination subject, wherein the deviation is identified taking into account the physiological movement.

14. The method of claim 12, further comprising receiving a dataset containing an image, a model, or the image and the model of the examination region, wherein the positioning information, the correction instruction, or the positioning information and the correction instruction are determined based on the dataset.

15. The method of claim 12, wherein determining the correction instruction comprises applying a trained function to input data, wherein the input data is based on the control instruction, wherein the input data is also based on the positioning information, the signal, or the positioning information and the signal, and wherein at least one parameter of the trained function is based on a comparison of a training correction instruction with a comparison correction instruction.

16. A method for providing a trained function, the method comprising:

receiving a training control instruction, wherein the training control instruction contains an instruction specified for a first movement of at least a predefined section of a medical object, wherein the medical object is holdable, movable, or holdable and movable using a mover device by transmission of a force in accordance with the training control instruction, and wherein the predefined section of the medical object is arrangeable in a training examination subject;

receiving training positioning information relating to a spatial positioning of the predefined section of the medical object;

receiving a training signal containing information relating to a counterforce acting in the opposite direction to the force, or a combination thereof;

identifying a training deviation between a movement state of the predefined section of the medical object and the first movement based on the training positioning information, the training signal, or the training positioning information and the training signal, the movement state of the predefined section of the medical object including a movement speed of the predefined section of the medical object;

determining a comparison correction instruction, wherein the determining of the comparison correction instruction comprises a simulation of movement trajectories of the predefined section of the medical object, wherein the movement trajectory that minimizes the training deviation is identified by a comparison, and wherein the comparison correction instruction comprises an instruction specified for a corrective movement of the predefined section along the identified movement trajectory;

determining a training correction instruction, the determining of the training correction instruction comprising applying the trained function to input data, wherein the input data is based on the training control instruction, wherein the input data is also based on the training positioning information, the training signal, or the training positioning information and the training signal;

adjusting at least one parameter of the trained function based on a comparison of the training correction instruction with the comparison correction instruction; and providing the trained function.

* * * * *